United States Patent
Rubinsky et al.

(10) Patent No.: US 8,361,391 B2
(45) Date of Patent: *Jan. 29, 2013

(54) VOLUMETRIC INDUCTION PHASE SHIFT DETECTION SYSTEM FOR DETERMINING TISSUE WATER CONTENT PROPERTIES

(75) Inventors: Boris Rubinsky, El Cerrito, CA (US); Cesar A. Gonzalez, Anahuac (MX)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/329,080

(22) Filed: Dec. 16, 2011

(65) Prior Publication Data

US 2012/0146621 A1 Jun. 14, 2012

Related U.S. Application Data

(63) Continuation of application No. 13/028,082, filed on Feb. 15, 2011, now Pat. No. 8,101,421, which is a continuation of application No. 12/616,102, filed on Nov. 10, 2009, now Pat. No. 7,910,374, which is a continuation of application No. 11/664,755, filed as application No. PCT/US2006/018384 on May 12, 2006, now Pat. No. 7,638,341.

(60) Provisional application No. 60/689,401, filed on Jun. 9, 2005.

(51) Int. Cl.
  *G01N 27/00* (2006.01)
  *G01N 33/48* (2006.01)
  *G01R 27/08* (2006.01)
  *G01R 25/00* (2006.01)

(52) U.S. Cl. ............... 422/82.01; 422/68.1; 422/82.02; 436/63; 436/149; 600/407; 600/547; 324/76.77; 324/692; 324/694

(58) Field of Classification Search ............... 436/63, 436/149, 174, 183; 422/68.1, 82.01, 82.02; 435/40.5; 600/407, 422, 437, 438, 442, 454, 600/456, 547; 324/76.77, 692, 694; 607/62

See application file for complete search history.

(56) References Cited

U.S. PATENT DOCUMENTS

| | | | |
|---|---|---|---|
| 4,008,712 | A | 2/1977 | Nyboer |
| 4,452,250 | A | 6/1984 | Chance et al. |
| 4,793,362 | A | 12/1988 | Tedner |
| 5,314,453 | A | 5/1994 | Jeutter et al. |
| 5,449,000 | A | 9/1995 | Libke |
| 5,807,272 | A | 9/1998 | Kun et al. |
| 6,585,660 | B2 | 7/2003 | Dorando et al. |
| 6,970,738 | B1 | 11/2005 | Othman et al. |
| 6,974,415 | B2 | 12/2005 | Cerwin et al. |
| 7,122,012 | B2 | 10/2006 | Bouton et al. |
| 7,638,341 | B2 | 12/2009 | Rubinsky et al. |
| 7,910,374 | B2 | 3/2011 | Rubinsky et al. |
| 8,101,421 | B2 | 1/2012 | Rubinsky et al. |

(Continued)

OTHER PUBLICATIONS

Gonzalez, C. et al., The detection of brain oedema with frequency-dependent phase shift electromagnetic induction, Physiological Measurement, vol. 27, (2006), pp. 539-552.

(Continued)

*Primary Examiner* — Maureen Wallenhorst
(74) *Attorney, Agent, or Firm* — Elizabeth A. Alcamo; Bozicevic, Field & Francis LLP

(57) ABSTRACT

A method and apparatus of determining the condition of a bulk tissue sample, by: positioning a bulk tissue sample between a pair of induction coils (or antennae); passing a spectrum of alternating current (or voltage) through a first of the induction coils (or antennae); measuring spectrum of alternating current (or voltage) produced in the second of the induction coils (or antennae); and comparing the phase shift between the spectrum of alternating currents (or voltages) in the first and second induction coils (or antennae), thereby determining the condition of the bulk tissue sample.

19 Claims, 9 Drawing Sheets

U.S. PATENT DOCUMENTS

2003/0229382 A1 12/2003 Sun et al.
2006/0264775 A1 11/2006 Mills et al.
2008/0306359 A1 12/2008 Zdeblick et al.

OTHER PUBLICATIONS

Griffiths, H., "Magnetic induction tomography," Measurement Science and Technology, vol. 12, (2001), pp. 1126-1131.

He et al., CN 1419889 abstract, May 28, 2003, 9 pages in length.

International Search Report for Application No. PCT/US2006/018384, dated Oct. 16, 2006.

Lin, J. et al., Microwave Imaging of Cerebral Edema, Proceedings of the IEEE, vol. 70, No. 5, May 5, 1982, pp. 523-524.

Riedel, C. H. et al., "Post mortem conductivity measurement of liver tissue using a contact free magnetic induction sensor," Proceedings of the 25th Annual International Conference of the IEEE EMBS, Sep. 17-21, 2003, pp. 3126-3129.

Scharfetter, H. et al., "Biological Tissue Characterization by Magnetic Induction Spectroscopy (MIS): Requirements and Limitations," IEEE Transactions on Biomedical Engineering, vol. 50, No. 7. Jul. 2003, pp. 870-880.

VOLUMETRIC INDUCTION PHASE SHIFT DETECTION SYSTEM FOR DETERMINING TISSUE WATER CONTENT PROPERTIES

CROSS-REFERENCE TO RELATED APPLICATIONS

The present application is a Continuation and claims priority to U.S. patent application Ser. No. 13/028,082, filed on Feb. 15, 2011, now U.S. Pat. No. 8,101,421 issued on Jan. 24, 2012; which is a Continuation of U.S. patent application Ser. No. 12/616,102, filed on Nov. 10, 2009, now U.S. Pat. No. 7,910,374, issued on Mar. 22, 2011; which is a Continuation of a U.S. national phase patent application Ser. No. 11/664,755, filed on Feb. 25, 2008, of the same title, now U.S. Pat. No. 7,638,341, issued on Dec. 29, 2009; which claims the benefit of a PCT application serial number PCT/US2006/18384, filed on May 12, 2006, of same title, and claims the benefit of Provisional patent application Ser. No. 60/689,401, filed on Jun. 9, 2005, entitled "Volumetric Induction Phase Shift Detection of Edema and Ischemia," the disclosures of which are hereby incorporated herein by reference in their entirety.

FEDERAL FUNDING

This invention was made with government support under NIH Grant No. RR018961 awarded by the National Institutes of Health. The government has certain rights in the invention.

TECHNICAL FIELD

The present invention relates to non-contact systems for assessing water content properties in bulk tissue, and identifying medical conditions associated with abnormal tissue water content properties.

BACKGROUND OF THE INVENTION (a) Medical Conditions Caused By Abnormal Tissue Water Content:

A variety of different medical conditions are associated with abnormal tissue water content. Examples of such medical conditions include, but are not limited to: edema (including brain edema), ischemia, internal bleeding (including intraperitoneal bleeding), dehydration, and extravasation.

A change in water content occurring in an organ or a tissue sample over time can be very indicative of a medical condition developing. As will be explained below, different systems have been developed to assess tissue water content properties (and changes in such conditions over time). Such systems can be particularly useful in diagnosing the onset of various medical conditions. However, as will be shown, existing systems all suffer from various disadvantages.

(b) Edema and Ischemia:

Tissue edema is a pathological condition involving an increase in the amount of fluid in tissue. The accumulation of fluid can be extracellular, intracellular or both. Extracellular edema is caused either by increased ultrafiltration or decrease in reabsorption. Intracellular edema can be caused by ischemia and the resulting intracellular hyperosmolarity or as a consequence of extracellular hypotonicity. Independent of the edema type, the condition is one in which the amount of liquid in the tissue increases and the balance is changed, usually as a function of time after an event has occurred. Tissue edema is of substantial concern when it occurs in the brain or in the lung. In the brain, extracellular edema develops in a delayed fashion, over a period of hours or days, after a large hemispheric stroke and is a cause of substantial mortality. Ischemic brain edema begins with an increase in tissue Na+ and water content and continues with blood brain barrier breakdown and infarction of both the parenchyma and the vasculature itself.

A study of the Center for Disease Control and Prevention for the period from 1995 to 2001 indicates that at least 1.4 million annual traumatic brain injuries occur in the USA alone. These resulted in about 1.1 million emergency department visits, 235,000 hospitalizations and about 50,000 deaths. About 1,100 incidents per 100,000 in population occur in the age group from 0 to 4 years. Head injury causes more deaths and disability than any other neurological condition under the age of 50 and occurs in more than 70% of accidents. It is the leading cause of death in males under 35 yr old. Fatalities may not result from the immediate injury; rather, progressive damage to brain tissue develops over time. In response to trauma, changes occur in the brain that requires monitoring to prevent further damage.

Brain swelling can be caused by an increase in the amount of blood to the brain. Brain edema is one of the most important factors leading to morbidity and mortality in brain tumors. Cerebral edema, which is an increase in brain volume caused by an absolute increase in tissue water content, ensues. The accumulation of fluid can be extracellular, intracellular or both. Vasogenic edema results from trans-vascular leakage often caused by the mechanical failure of the tight endothelial junction of the blood-brain barrier and increased ultrafiltration or decrease in re-absorption. Vasogenic edema also results from extravasation of protein rich filtrate in interstitial space and accumulation of extracellular fluid. Cytotoxic edema is characterized by cell swelling. Cytotoxic edema is an intracellular process resulting from membrane ionic pump failure. It is very common after head injury and it is often associated with post-traumatic ischemia and tissue hypoxia. The primary mechanism is reduction of sodium-potassium ATPase pump efficiency due to local hypoxia and ischemia. This type of edema occurs in cancer with compression of microcirculation. Interstitial or hydrocephalic edema occurs when there is an accumulation of extracellular fluid in the setting of hydrocephalus. Intraventricular tumors or tumors that constrict ventricles can cause this type of edema.

Independent of the edema type, the condition is one in which the amount of liquid in the tissue increases or the balance is changed. Edema is of substantial concern when it occurs in the brain. The characteristics of brain edema, is that it develops in a delayed fashion, over a period of hours or days, after the brain trauma has occurred and is a cause of substantial mortality. Detection and continuous monitoring of edema in the brain is essential for assessment of medical condition and treatment.

Pulmonary edema is often associated, with lung injury and also requires continuous monitoring and treatment. Detection and continuous monitoring of edema in the brain and lung is useful for assessment of medical condition and treatment.

Ischemia of tissues and organs is caused by a change in normative physiological conditions such as deprivation of oxygen and blood flow. It can occur inside the body, for instance as a consequence of impediments in blood flow. Ischemia also can occur outside the body when organs preserved for transplantation are transported. Ischemia results in changes in the intracellular composition which is accommodated by changes in the water content properties of the intracellular and extracellular space and leads to cell death.

Therefore, in medical applications it is important to be able to detect changes in water content properties which are indicative of the occurrence of edema and ischemia.

(c) Internal and Interperitoneal Bleeding:

Trauma is the third most common cause of death in all age groups and the leading cause of death in the first three decades of life. Of all traumatic injuries abdominal and pelvic injuries contribute to about 20% of the fatalities. In addition, death from abdominal hemorrhage is a common cause of preventable death in trauma patients. Bleeding is the cause of one in four maternal deaths worldwide. Death may occur in less than two hours after the onset of bleeding associated with childbirth. In addition to trauma, abdominal bleeding also occurs in several post-surgery conditions. Unfortunately, early intraperitoneal bleeding cannot be detected by vital signs (rate pulse or blood pressure) and it becomes evident only after a critical amount of blood has found its way into the abdominal cavity. Therefore, death from abdominal hemorrhage is a common cause of preventable death in trauma patients. However, early detection of intraperitoneal bleeding may play a critical role in the patient survival.

(d) Extravasation:

Extravasation is the unwanted passage or escape of blood, serum, lymph or therapeutic drugs directly into body tissues. Signs and symptoms may include the sudden onset of localized pain at an injection site, sudden redness or extreme pallor at an injection site, or loss of blood return in an intravenous needle. Extravasation can lead to skin and tissue necrosis, and "Compartment Syndrome" (a pathologic condition caused by the progressive development of arterial compression and reduction of blood supply).

Similar to the medical conditions described above, extravasation results in a change in water content properties in the tissue (typically at or near an injection site). Thus, it would be desirable to detect extravasation, (preferably by a on-contact system). Unfortunately, no such system currently exists.

(e) Existing Systems for Assessing Tissue Water Content Properties—and Their Limitations:

Accumulation of fluid in tissue changes the electrical impedance of the tissue. This has suggested the use of bioelectrical impedance measurements to detect water content in the body since 1962. Edema and ischemia can be also detected with bioelectric measurements. With edema or ischemia, the ratio between extracellular and intracellular water changes. Since this should cause a shift in the beta dispersion frequency, bioimpedance spectroscopy based on measuring the changes in the overall impedance has been viewed as a likely way to produce information on edema and ischemia.

Another important method to evaluate and monitor edema is Electrical Impedance Tomography (EIT). En uses an array of electrodes (placed on the patient) to inject subsensory currents and measure the resultant voltages. The data is used to reconstruct a map of the electrical impedance of tissue. Unfortunately, a problem with electrical impedance tomography (EIT) is that it requires the placement of needles in contact with the tissue. Furthermore, EIT produces an image of the area showing the location of the change in water content properties. This is a time consuming process. In addition the details produced by imaging may not be needed in many applications of detection of water content properties.

Another way to detect edema and ischemia is by performing induction tomography. In this approach, induction currents rather than injection currents are used to produce a map of the electrical properties of tissue. The problem with this method is that the induction coils need to be large, i.e. are much larger than electrodes, and there are difficulties with using large number of coils for good imaging resolution. Furthermore the imaging outcome has the same overall attributes as EIT in regards to detection of edema and ischemia. In general, imaging and tomography are expensive and require many measurements. In the past, direct impedance measurements of ischemia have been used to assess the condition of organs preserved for transplantation. However as with EIT, this requires the placement of needles on the organ or tissue. This is cumbersome with organs and impossible in such tissues as the brain and the lungs or large volumes of the abdomen.

Tumor associated edema is visible on both CT and MRI. Unfortunately, the diagnostic is complicated by the fact that on CT it produces low signal, which can be confused with low-signal producing tumors. On MRI, the edematous brain produces a hypersignal, which may be confused with hypersignal producing tumors.

With regard to diagnosing abdominal injuries, there are two methods for rapid detection of intraperitoneal bleeding, FAST (focused assessment with sonography for trauma) ultrasound and peritoneal lavage. Evaluations of the practice in the evaluation of internal injuries show that physicians prefer to use FAST ultrasound over diagnostic peritoneal lavage (DPL) because DPL is invasive and most doctors have limited experience in DPL and interpreting the results. However, rural hospitals rarely have advanced imaging modalities such as CT scan or emergency ultrasound. As a result, emergency physicians in such centers are forced to rely on clinical examination and plain radiography alone. The lack of advanced imaging may delay the identification of patients who require transfer, or lead to inappropriate transfer of patients who are later found not to require trauma centre intervention.

In addition, most of the current bioelectronic techniques for detection of abdominal bleedings try to produce an image or information that will determine the site of bleeding. However, currently in the medical emergency departments initial evaluation and treatment is not geared towards identification of a specific abdominal injury, but rather to determine if one exists.

SUMMARY OF THE INVENTION

The present invention provides an electrical measurement system that conveniently produces bulk information on the properties of organ or tissue. In preferred aspects, the present invention uses bioimpedance analysis based on the conduction of an applied electrical current in the tissue to detect a variety of medical conditions.

In one aspect of the invention, the present system provides a non-contact method for detecting tissue properties in a volume of tissue by measuring change in electromagnetic induction spectroscopic distribution of phase shift over time. Thus, instantaneous bulk measurements of the electrical properties of an organ or tissue sample can be made with induction currents. In another aspect of the invention, the present system provides a non-contact method for detecting changes in tissue properties in a volume of tissue by measuring change in electromagnetic induction spectroscopic distribution of phase shift over a period of time.

In either of the above instantaneous "snapshot" aspect approach, or the measurement of changes occurring over time approach, measurements are made detecting phase shift between the applied and measured currents. Specifically, a change is detected in the phase angle between the AC currents in an emitting and a sensing induction coil or antenna. This phase shift is caused by a volume of tissue placed between the emitting and a sensing coil or antenna through which AC currents are passed over a wide range (i.e.: spectrum) of frequencies.

As will be shown below, the present invention provides a spectroscopic measuring method that is simpler and more reliable than overall impedance measurement. In addition, the present invention provides a system of measuring the electromagnetic change in water content properties in the bulk would suffice for many applications.

The present invention can thus be use to evaluate the medical condition of a volume of biological tissue by assessing the bulk tissue electrical properties of the volume of tissue, and determining how they change over time.

There are numerous advantages to the present invention, including, but not limited to, the following:

First, the present invention does not require galvanic coupling between the electrode and the skin or the tissue under measurement. Instead, the present system is completely non-invasive. As a result, it is easy to operate. Moreover, it is inexpensive to build and to operate. Thus, the present invention can be operated in locations and conditions such as remote villages, traffic accidents or military engagement in which there is no full medical service.

Second, measuring change in phase shift in the bulk of tissue, body or organ with time is a simple measurement that focuses only on the occurrence of changes in a particular frequency or range of frequencies. Thus, the present system of bulk detection has the advantage of low cost and ease of use while still providing relevant data.

Third, a further advantage of the present system is that instantaneous measurement of the phase shift can be made. Alternately, however, time dependent measurements can also be made to detect the progress of the phase shift in time to determine the development of the medical condition Fourth, the present invention is especially well suited to detect edema in the brain since the skull does not represent a barrier for the electro-magnetic field at certain frequencies.

Fifth, while imaging the body or the organ may be of importance, very often in clinical practice it is sufficient simply to know that there is a problem occurring (and to alert the physician to the occurrence). I.E.: to determine that there is edema (or bleeding, or other conditions) in a certain organ or parts of the body; such as the brain the abdomen or the lung or that extravasation or dehydration are taking place. Furthermore, there are many applications in which it is sufficient to have a general estimate of the occurrence of ischemia and not the precise location of the ischemic tissue. For instance, in organ transplantation it is important to know that the organ is functional or not and not the degree of functionality of the different parts of the organ. Accordingly, the present system of bulk measurement indications of the occurrence of edema or ischemia may be sufficient for many clinical many applications.

In one aspect, the present invention provides a method of determining the condition of a bulk tissue sample, by: positioning a bulk tissue sample between a pair of induction coils or antenna; passing a spectrum of alternating current through a first of the induction coils; measuring spectrum of alternating current produced in the second of the induction coils; and comparing the phase shift between the spectrum of alternating currents in the first and second induction coils, thereby determining the condition of the bulk tissue sample.

In another aspect of the method, the present invention comparing the phase shift between the spectrum of alternating currents in the first and second induction coils over time, thereby determining a change in the condition of the bulk tissue sample over time.

In another aspect, the present invention provides an apparatus for determining the condition of a bulk tissue sample, comprising: a first induction coil; a second induction coil; an alternating current power supply connected to the first induction coil, the alternating current power supply configured to generate a spectrum of currents in the first induction coil; and a measurement system connected to the second induction coil, wherein the measurement system is configured to measure a phase shift difference in the spectrum of currents or voltages between the first and second induction coils when the first and second induction coils are positioned in relation to each other and of a tissue sample or organ or body parts.

In another aspect, the present invention provides an apparatus for determining the condition of the bulk tissue sample, comprising: a first antenna; a second antenna; a high frequency electromagnetic waves supply to generate a spectrum of electromagnetic waves in the first antenna; and a measurement system connected to the second antenna, wherein the measurement system is configured to measure a phase shift difference in the spectrum of currents or voltages between the first and second induction antennae when the first and second induction antenna are positioned in relation to each other and of a tissue sample or organ or body parts.

The present invention has been experimentally validated to show that it can detect ischemia and/or edema and/or intraperitoneal bleeding.

The present system can be used on a wide variety of tissues, including, but not limited to brain tissue, lung tissue, heart tissue, muscle tissue, skin tissue, kidney tissue, cornea tissue, liver tissue, abdomen tissue, head tissue, leg tissue, arm tissue, pelvis tissue, chest tissue or trunk tissue.

In some aspects of the invention, the frequency range of the alternating current is from 10 kHz to 10 GHz. In one aspect, a more preferred range is from 1 MHz to 10 GHz. The present invention can be used with coils or antenna. One preferred range for use with coils is from 10 kHz to 1 GHz, with a more preferred range being from 10 kHz to 300 MHz. One preferred range for use with antennae is from 100 MHz to 10 GHz, with a more preferred range being from 300 MHz to 10 GHz.

Figure 1:
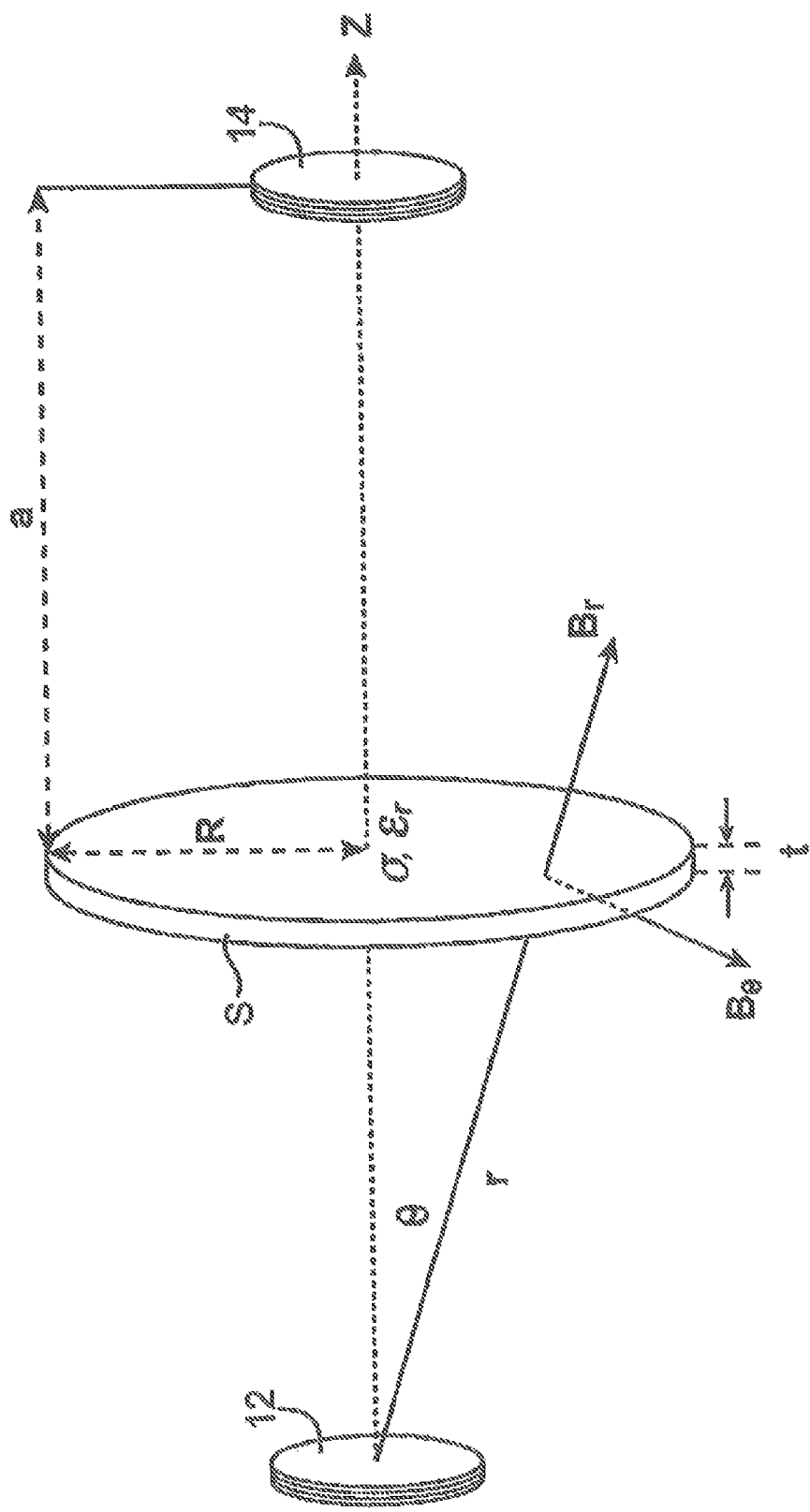
FIG. 1 is a simplified schematic of the present invention, showing a tissue sample positioned between a pair of induction coils.

DETAILED DESCRIPTION OF THE DRAWINGS (a) Theory:

As stated above, the present system assesses tissue condition by determining volumetric bulk properties of the water content of the tissue. Specifically, the sensing of an induction phase shift is used to assess tissue condition.

Biological tissues contain compounds with measurable electrical properties such as the intracellular and extracellular ionic solutions, the capacitative cell membrane, charged macromolecules and polar water. The combination of these compounds in terms of composition and structure affect the overall electromagnetic properties of the tissue. The particular effect of each one of these components and combinations is affected in a different way as a function of the electromagnetic field excitation frequency and magnitude applied on the tissue. Typical spectroscopic behavior of certain tissues is illustrated in the 100% blood, brain, muscle and lung curves in FIG. 2 (the other curves in the figure will be discussed later). The overall effect of excitation frequency on the electromagnetic properties is well understood since the pioneering work of Schwan (Schwan, H. P. (1957). "*Electrical properties of tissue and cell suspensions*." Adv. Biol. Med. Phys. 5: 147-209.) Reviews can be can be found in many texts on the topic: S. Grimnes and O. G. Martinsen, *Bioimpedance and Bioelectricity Basics*. San Diego, Calif.: Academic Press, 2000, pp. 87-124; K. R. Foster and H. P. Schwan, "Dielectric properties of tissues" in *Biological Effects of Electromagnetic Fields*. Boca Raton, Fla.: CRC Press, 1996, pp. 27-106. Briefly, body tissues contain intra and extracellular fluids that behave as electrical conductors and cell membranes that act as electrical capacitors. At DC and low frequencies electrical current passes mainly through the extracellular fluid; at higher frequencies, however, current penetrates both intra and extracellular fluids. Therefore, body fluids and electrolytes are responsible for electrical resistance and cell membranes for reactance. At MHz frequencies the impedance of proteins becomes important and at GHz frequencies the behavior of water is sampled. In particular, up to roughly about 100 MHz the behavior should be affected by Maxwell Wagner relaxation of membranes, proteins in water and bound water whereas above about 100 MHz it should depend on the relaxation of free water, ionic conductivity and bound water. The increase in conductivity in the tissue as a function of the GHz frequency arises from the rotational relaxation of the water dipoles in tissue. In this sense, at higher frequencies the observations depend on the net water content in a volume rather than the cellular structure.

The relation between water and tissue content and properties and complex electromagnetic properties occurs throughout the frequency domain. Accordingly, the present system can be used to detect changes in tissue water properties with phase shift in a broad range of frequencies from kHz to GHz. Since the measurement of interest is phase shift in the bulk of tissue or organs there are several considerations in choosing the appropriate frequency and apparatus involving the significance of what is measured and the dimensions that can be measured. Since the interest is in phase shift DC type of measurements are not of interest for this type of measurement. Theoretically it is anticipated that in the frequency range from about 100 kHz to 1 GHz, depending on the type of tissue, the phase shift measurement will be affected by both the relative distribution between the intracellular water and the extracellular water and the relative amount of water. Therefore this range would be useful in detecting such conditions as ischemia, edema, bleeding, extravasation, dehydration. The effects of change in water content between the intracellular and extracellular would be most pronounced between 1 MHz and 400 MHz, with the most sensitive measurements between 1 and 100 MHz. Phase shift measured at the higher frequency range from about 300 MHz to 10 GHz would be most sensitive to water content and would be sensitive to detect edema, bleeding and dehydration. In particular the range of 1 GHz to 10 MHz would be most sensitive to water content. However, in addition to the sensitivity of various tissues to frequencies, which are tissue and condition dependent, since the method involves measurement in the bulk of tissue organs and the body the penetration depth of the various electromagnetic wave frequencies is of importance. For instance the penetration depth of microwave frequency energy at between 1 GHz to 3 GHz is about 2 to 10 cm for soft tissue. Therefore the particular application of the measurement would relate the integration depth with the measurement frequencies.

(b) Simplified Representation of the Invention:

The present invention deals with a method and an apparatus for detecting phase shift due to tissue water properties in the bulk of tissue. The method and the apparatus require an emitter of electromagnetic waves and a receiver to be placed in relation to the bulk tissue to be analyzed. When working in the frequency domain electromagnetic coils are used for emitters and receivers in the frequency range of up to 400 MHz. Beyond about 400 MHz to several GHz range, antennae (such as microwave antennae) may be used. In the range of frequencies from about 300 MHz to 1 GHz, both coils and antennae could be used.

FIG. 1 is a simplified schematic of the present invention, as follows.

System 10 consists of two induction coils 12 and 14 with the organ or the part of the body (sample S) to be analyzed placed in a determined relation to the coils. It is to be understood that coils 12 and 14 can be replaced with antennae when operating at higher frequencies. Reference herein is made to coils, However, the present invention is not so limited as antennae can be used instead. Coil 12 is driven by an AC current power supply (not shown) while the current in the other coil 14 is produced by induction and measured. The properties of the material (sample S) between coils 12 and 14 determine the currents in the induction current coil 14. By comparing the voltages in first coil 12 to those in second coil 14, a measure of the bulk electrical properties of the tissue (sample S) there between can be made. In preferred embodiments, the present invention measures the difference in the phase between the two AC voltages, i.e. the "phase shift". In alternate aspects of the invention, a spectrum of voltages is passed through coil 12, and a current phase shift is measured in coil 14.

(c) Mathematical Model:

Different mathematical models are used to describe the system of this invention. The various mathematical models depend on the frequency analyzed. In the frequency range of up to about 1 GHz, more rigorously up to 300 MHz a quasistatic assumption can be made. In this range a solution such as that by (Griffiths, Steward et. al., Magnetic Induction Tomography—A Measuring System for Biological Materials" Ann. NY Acad. Sci. 873:335-345) can be used for analyzing the phase shift due the water content properties of tissue. In frequencies above that range the wave propagation becomes important and the eddy currents are not constant and an analysis of the type described in the same book but on page 327 is applied.

(i) Theoretical Considerations:

The analysis here follows Griffiths and his colleagues (See: Griffiths, Steward et. al., Magnetic Induction Tomography—A Measuring System for Biological Materials" Ann. NY Acad. Sci. 873:335-345). We consider as a simple case study tissue sample S to be a circular disk of tissue of radius R and thickness t, placed centrally and midway between a small excitation coil and a small sensing coil spaced at a distance 2a (See FIG. 1). The thickness t, was considered to be much less than 2a. A sinusoidal current, of angular frequency w, flows in excitation coil 12 and induces a magnetic field B. The circular non-magnetic tissue sample S has conductivity $\sigma$ and relative permittivity $\in_r$ (it is assumed that the skin depth is greater than, t, and therefore the attenuation produced by the disk is neglected).

Our bulk model of edema assumes that the edema is uniformly distributed in the tissue and that the occurrence of edema will cause the bulk electrical parameters of the combined tissue to change according to the formula:

$$\sigma_c(T, F) = \frac{\lfloor (\sigma_t \cdot T) + (\sigma_f \cdot F) \rfloor}{100} \quad (1)$$

$$\varepsilon_{r,c}(T, F) = \frac{[(\varepsilon_{r,t} \cdot T) + (\varepsilon_{r,f} \cdot F)]}{100}$$

where the subscripts c, t, and f stand for the composite properties, the tissue properties and fluid properties, respectively. The symbols, T, and, F, give the percentage volume of the pure tissue or the pure fluid respectively. In accordance with experiments performed by the Applicants in testing present invention, the tissue and fluid data used were taken from Gabriel and Lau (See: "The Dielectric Properties of Biological Tissues: III. Parametric Models for the Dielectric Spectrum of Tissues" Phys. Med. Biol. 41:2271-2293, 1996) and Duck (See: "Physical Properties of Tissue", London, Academic press, 1990, Chapter 6, 167 223.) In accordance with experiments performed by the Applicants in testing present invention, blood was considered as the edematous fluid for brain and muscle tissues; and human serum was considered for lung tissue.

Figure 2A:
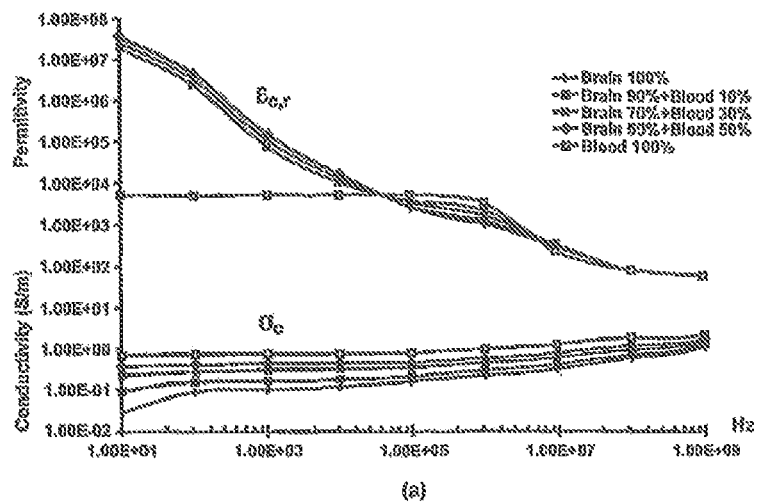
FIGS. 2A, 2B and 2C show calculated bulk electrical parameters as a function of frequency for various ratios of normal tissue to edema.
Figure 2B:
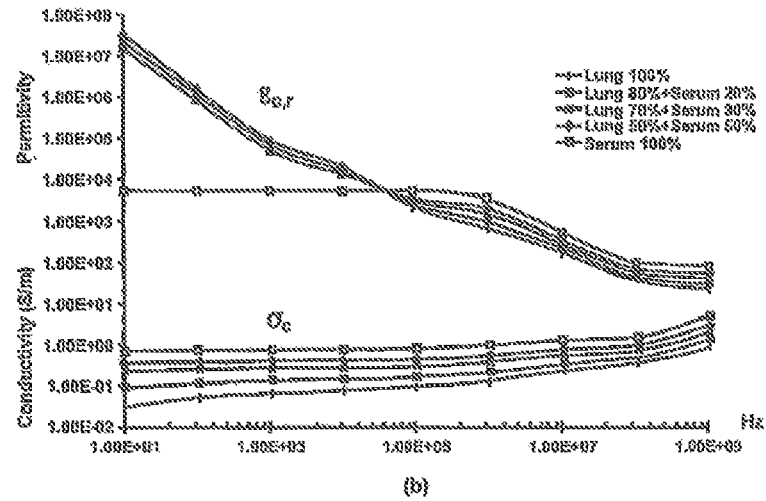
Figure 2C:
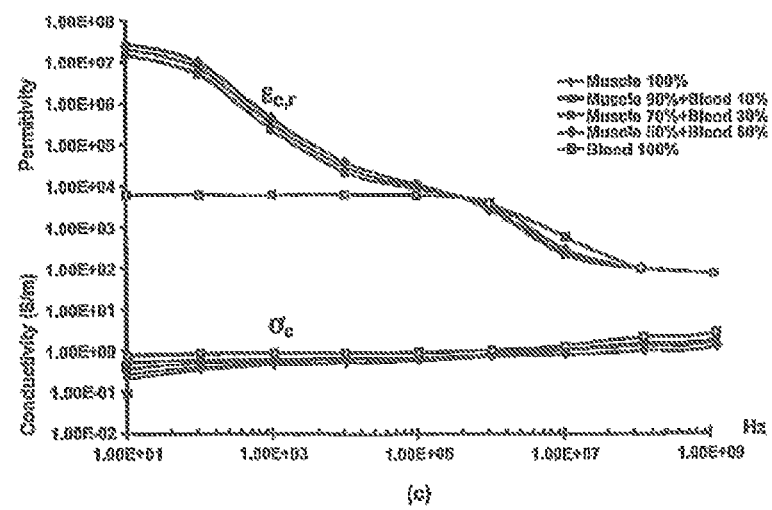

FIGS. 2A, 2B and 2C show the bulk electrical parameters as a function of frequency for various ratios of normal tissue to edema calculated from Eqs. (1) and the data in Garbriel and Lau, and Duck, supra. FIG. 2A shows brain tissues, FIG. 2B shows lung tissues and FIG. 2C shows muscle tissues. As expected; three typical major dispersion regions are observed for all the ratios tissue/fluid. For the cases of brain and muscle tissues the bulk electrical conductivity of all the ratios tissue/fluids have similar values as the frequency approaches 1 GHz. It's evident that at high frequencies the electrical properties of brain, muscle and blood become essentially the same. This fact can be attributed to the γ dispersion region where the dielectric properties of the tissue are dominated by the water content. In contrast; for the case of lung tissue the bulk electrical parameters of all the ratios tissue/fluids have different values in the whole bandwidth. This behavior can be explained by the different electrical properties of the human serum with respect to the lung tissue.

(ii) Phase Shift in Sensing Coil 14:

Considering the thin "tissue" disk model described above, a sinusoidal current of angular frequency ω, flows in excitation coil 12 and induces a magnetic field B in sensing coil 14. According to Griffiths, supra, the current induced in the "tissue" disk (sample S) placed between the excitation coil 12 and the sensing coil 14 causes a perturbation ΔB in the field of the sensing coil given by:

$$\frac{\Delta B}{B} = (\omega \varepsilon_o \varepsilon_r - j\sigma) \left( \frac{ta^3 \omega \mu_o}{2} \right) \left\{ \frac{1}{a^2} - \frac{a^2 + 2R^2}{(a^2 + R^2)^2} \right\} \quad (2)$$

where $\in_0$ and $\mu_0$ are the permittivity and permeability of free space, respectively. The total magnetic field B+ΔB in sensing coil 14 is shifted relative to the primary magnetic field B by an angle θ. The magnetic field and its perturbation can be obtained from the voltages induced in the sensing coil, $V_i$ and $\Delta V_i$. ΔB/B can be defined in terms of the induced voltage in sensing coil 14, by:

$$\frac{\Delta B}{B} = \frac{\Delta V_i}{V_i} \quad (3)$$

We define a constant k:

$$k = \left( \frac{ta^3 \mu_o}{2} \right) \left\{ \frac{1}{a^2} - \frac{a^2 + 2R^3}{(a^2 + R^2)^2} \right\} \quad (4)$$

Substituting (3) and (4) into (2), the phase of the total induced voltage $\theta(V_{ind})$ in sensing coil 14 with respect to the induced voltage by the primary magnetic field in coil 14 could be expressed as a function of frequency and electrical parameters in the "tissue" disk between the coils [16], by:

$$\theta(V_{ind}) = \arctan\left( \frac{k\omega\sigma}{k\omega^2 \varepsilon_0 \varepsilon_r + 1} \right) \quad (5)$$

Figure 3:
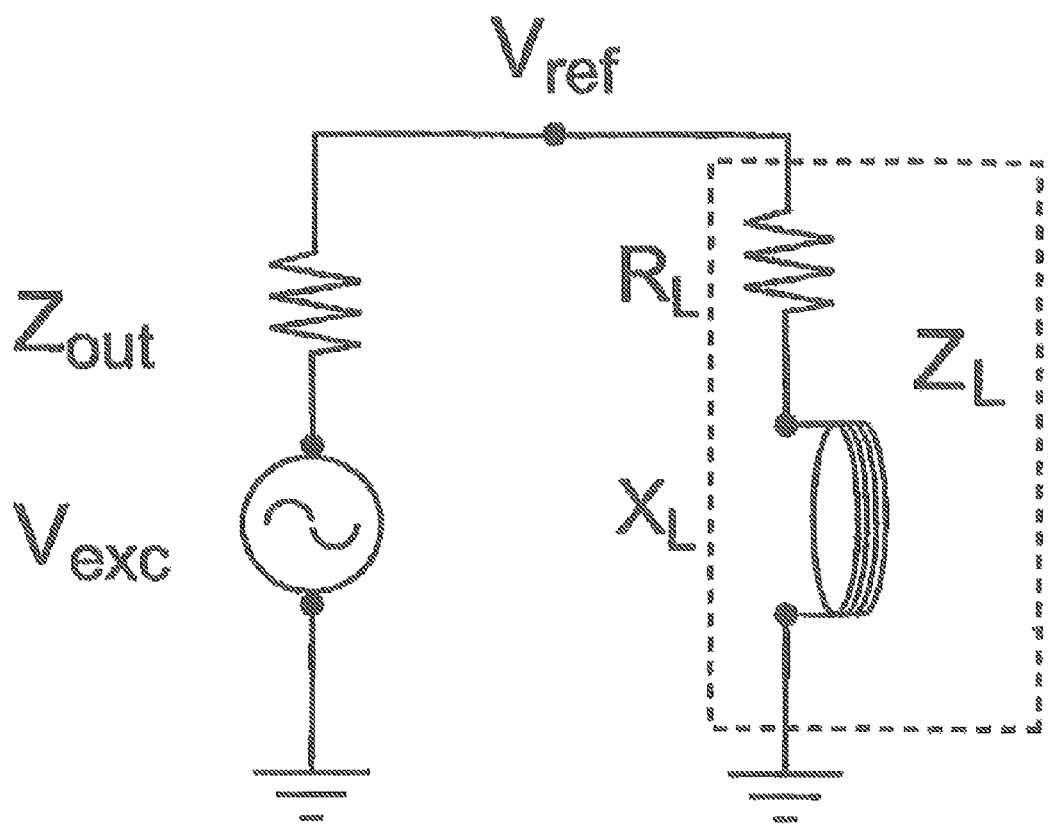
FIG. 3 is a schematic of a device for electro-magnetic field generation.

(ii) Phase Shift in Excitation Coil 12:

The magnetic field in the present invention can be generated in the device as shown in FIG. 3. Specifically, an oscillator supplies an excitation signal ($V_{exc}$) through an output impedance, $Z_{out}$. The reference voltage ($V_{ref}$) measured in the excitation coil is given by expression (6) where $Z_L$ is the impedance of a coil composite made of the resistance $R_L$ and the inductance $X_L$, in series.

$$V_{ref} = V_{exc}\left( \frac{Z_L}{Z_{out} + Z_L} \right) \quad (6)$$

According to Hart L. et al. (See: A noninvasive electromagnetic conductivity sensor for biomedical applications" IEEE Trans Biomed Eng 32(12): 1011-1022, 1988), the presence of a conductive sample (the "tissue" disk between the coils) causes a change in the impedance of the excitation coil given by $\Delta Z_L = \Delta R_L + \Delta X_L$, where: $\Delta R_L$ is the increase in the coil resistance and $\Delta X_L$ is the increase in the coil inductance. The expressions for $\Delta R_L$ and $\Delta X_L$ were derived in Hart et. al., supra as:

$$\Delta R = 32\pi^3 * 10^{-14} N^2 f^2 R'^3 l' \Delta \sigma \quad (7)$$

$$\Delta X = 64\pi^4 * 10^{-14} N^2 f^2 R'^3 l' \in_0 \Delta \in_r \quad (8)$$

where: f=ω/2π is the frequency of the excitation signal, N is the number of coil turns, R' is the coil radius, $\in_0$ is the permittivity of free space, and $\in_r$ and σ are the relative permittivity and electrical conductivity of the "tissue" disk sample respectively. The term is a positive definite constant determined for a specific geometry and several approximations are given in Hart et. al., supra. In this study substitutions of $\sigma_c \rightarrow \Delta\sigma$ and $\in_{r,c} \rightarrow \Delta\in_r$ were made for the expressions (7) and (8) because changes in electrical conductivity and relative permittivity of the "tissue" sample are considered.

The phase of the reference voltage $\theta(V_{ref})$ with respect to the excitation signal in the presence of a "tissue" sample can be estimated from the following expression:

$$\theta(V_{ref}) = \arctg \left[ \frac{\text{Im}\left[\frac{Z_L + \Delta Z_L}{Z_{out} + Z_L + \Delta Z_L}\right]}{\text{Re}\left[\frac{Z_L + \Delta Z_L}{Z_{out} + Z_L + \Delta Z_L}\right]} \right] \quad (9)$$

Later in this study, the analysis for estimation of phase shift with edema was performed by using tissue properties from the experimental data in Gabriel and Duck, supra, and from the solution of equation (5) and (9) with the bulk properties from equation (1). The total change in phase shift (Δθ) between the reference and induced voltages in the excitation and sensing coil respectively is given by the expression:

$$\Delta\theta = \theta(V_{ind}) - \theta(V_{ref}) \quad (10)$$

Figure 4:
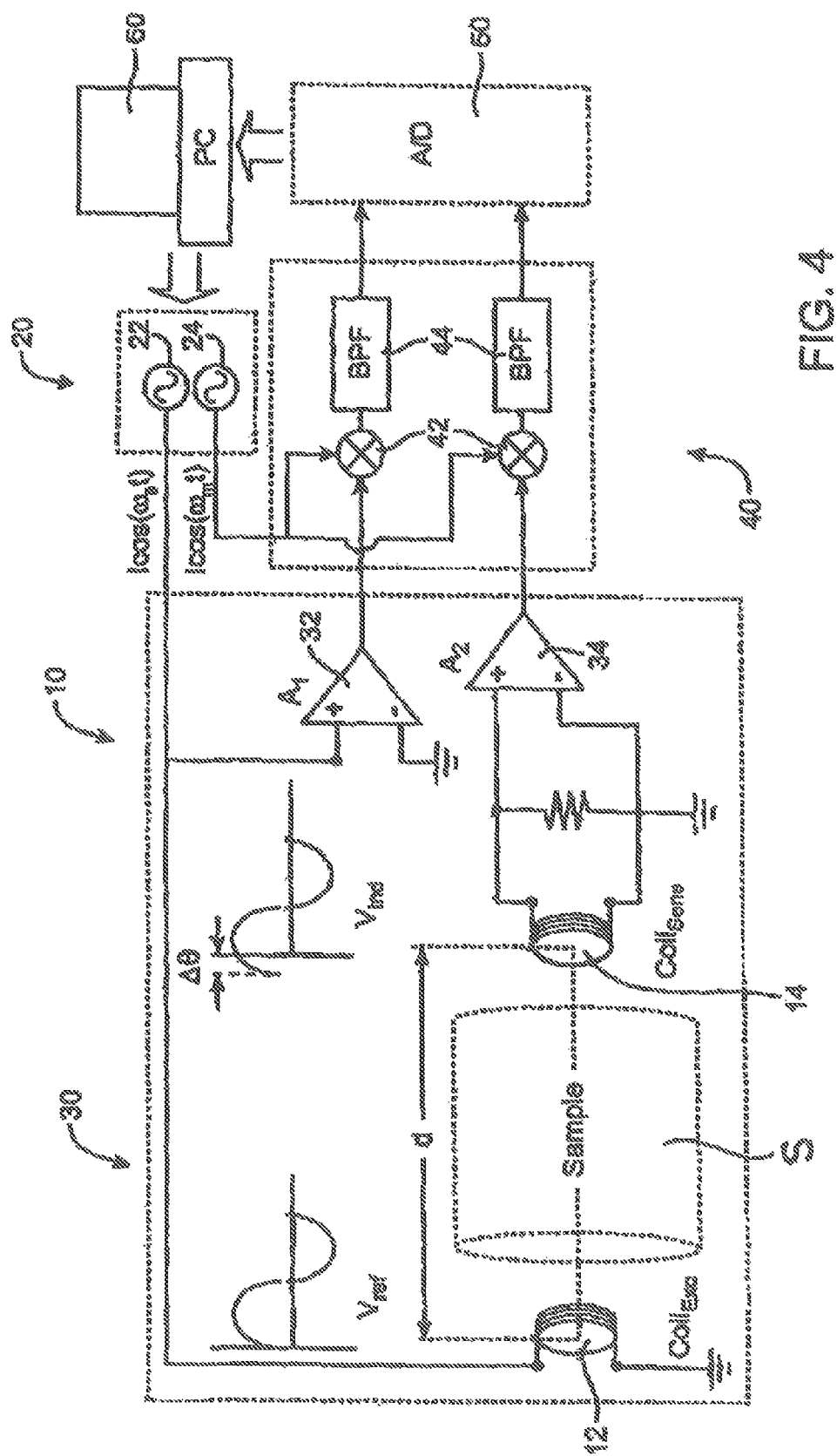
FIG. 4 is a multi-frequency inductive phase shift detection spectrometer in accordance with the present invention.

(d) Experimental System:

FIG. 4 illustrates a multi-frequency inductive spectrometer system 10 as designed, constructed and operated by the Applicants. This system is preferably used for a frequency of up to 400 MHz. System 10 comprises four modules: function generator 20, transceiver 30, dual-channel demodulator 40 and analog digital converter 50. A personal computer 60 with a Pentium 2 GHz processor (model 4400, Dell Inc. Round Rock, Tex.) controls the system and processes the data.

Function generator 20 uses two identical programmable synthesizers 22 and 24 (NI 5401, National Instruments Inc, Austin, Tex.) as oscillators. Oscillator 22 supplies an excitation signal I $\cos(\omega_e t)$ of approximately 20 mA in the range of 1 to 8 MHz at pre-programmed steps. A modulation signal I $\cos(\omega_m t)$ is generated by second oscillator 24. The difference $\omega_e - \omega_m = \omega_o = 100(2\pi)$ rad/sec is maintained constant in the whole bandwidth in order to produce a narrow band measured voltage signal on a constant low intermediate frequency for processing and demodulation, as proposed by Ristic, B. et al. (See: "Development of an impredance spectrometer for tissue monitoring: application of synchronous sampling principle" Proc 21st IEEE Annual Northeast Conference, 22-23 May, 1995, pages 74-75).

The excitation and modulation signals are connected to transceiver 30 and dual-channel demodulator 40 modules respectively. Transceiver 30 consists of an excitation coil 12 and a sensing coil 14 coaxially centered at a distance d=10 cm and two differential receiver amplifiers 32 and 34 (AD8130, Analog Devices Inc. Norwood, Mass.). Both coils 12 and 14 were built with magnet wire AWG32 rolled on a cylindrical plastic former with radius r=2 cm, five turns. The coil inductance, as calculated on the basis of Faraday's law, is approximately 40 µH. The excitation coil 12 generates a primary oscillating magnetic field. The sensing coil 14 detects the primary magnetic field and its perturbation through a proximal conductive tissue sample S. To avoid inductive pickup the leads of the coils are twisted. The amplifiers 32 and 34 were connected as conventional operational amplifiers and collect the reference voltage ($V_{ref}$) and the induced voltage ($V_{ind}$) in the excitation 12 and sensing 14 coils respectively. The gain of amplifiers 32 and 34 was adjusted in order to obtain a dynamic range of ±5V throughout the whole bandwidth.

Dual-channel demodulator 40 uses a pair of mixers 42 and narrow band pass filters 44 to transfer the information of any excitation and sensing signal of a variable frequency to a constant low frequency ($\omega_o$). A multiplier (AD835, Analog Devices Inc. Norwood, Mass.) was used as mixer 42. Narrow band pass filter 44 was designed on the basis of operational amplifier 32 (AD844, Analog Devices Inc. Norwood, Mass.). This module used two identical channels for parallel demodulation.

To avoid additional inductance and stray capacitance in the circuit, amplifiers 32 and 34 and dual channel-demodulator circuits 40 were shielded by a metallic box and connected to coils 12 and 14 with short coaxial cables (length less than 0.8 m). The current passes through the shield to minimize any inductance mutual between the circuit and the coils.

Analog-digital conversion module 50 digitized the reference and induced voltage signals on the constant low frequency. A data acquisition card NI 6071E (National Instruments Inc, Austin, Tex.) with a sample rate of 1.25 MSamples/seg and a resolution of 12 bits was used as analog-digital converter 50. The phase of the reference and induced voltages were calculated in software over approximately five cycles by an extract single tone function available in LAB VIEW V 6.1 (National Instruments Inc, Austin, Tex.). This function was programmed to find the highest amplitude at $100(2\pi)$ rad/sec and return the phase. The phase shift between the reference and induced voltage was estimated as $\Delta\theta = \theta(V_{ind}) - \theta(V_{ref})$. The ratio signal to noise (SNR) for phase shift measurement was improved by averaging over twenty spectra (39 dB at 1 MHz).

For use up to higher frequencies including GHz range the present apparatus may comprise of a source of electromagnetic energy such as an RF Signal generator (Agilent 8648D9 KHz-4 GHz. The source is connected to an emitter which is a single frequency commercial antenna for microwave or radiofrequency placed in relation to the analyzed tissue and another similar receiving antenna. The receiving antennae is connected to an amplifier such as (Low Noise Amplifier, Agilent 11909A, 9 KHz-1 GHz), or (Microwave system amplifier Agilent 83006A10 MHz-26.5 GHz). The signal and the phase shift can be detected with Agilent 4396B RF Network/Spectrum/Impedance Analyzer, 100 kHz to 1.8 GHz).

(e) Experimental Results—Detection of Interperitoneal Bleeding in Rats:

Intraperitoneal bleeding in the abdomen of a rat was simulated by infusion of various volumes of physiological saline into the abdominal cavity in rats. Specifically, experiments were performed identically on each of five rats. The experiments started with anesthetization of the animal via intraperitoneal injection of Nembutal solution (50 mg/ml sodium pentobarbital, Abbot Labs, North Chicago, Ill.) for a total of 100 mg sodium pentobarbital per kg of rat. To simulate intraperitoneal bleeding and accumulation of fluids in the abdomen we injected various volumes of physiological saline (0.9% w/w NaCl) into the abdominal cavity through a short intravenous catheter (Venflow). The catheter remained in place throughout the experiment. We injected increasing volumes of saline and the measurements were done for four volumes of: 1, 2.5, 5 and 7.5% of (weight of saline)/(weight of the tested rat). The physiological saline was maintained at approximately 36.5° C. prior to injection. In all the experiments the baseline reference measurement was for the experimental subject prior to the intraperitoneal physiological saline injection. In all the experiments the coils were placed around the abdomen of the rat in such a way that the abdominal cavity was centered between the excitation and sensing coils. The geometrical position was carefully maintained as similar as possible for all the subjects.

The Applicants studied the phase shift due to four different volumes of saline in the frequency range from 1 MHz to 8.5 MHz with an induction system for measuring bulk phase shift. As will be shown below, the test results show that inductive bulk measurements of phase shift are sensitive to the relative volume of saline at frequencies higher than approximately 1 MHz, which is qualitatively consistent with our theoretical predications. In addition, the phase shift detected increases as a function of frequency and the fluid volume also qualitatively consistent with the theoretical predictions. As such, the results indicate that bulk induction measurement of the phase shift has the potential for becoming a robust means for non-contact detection of intraperitoneal bleeding.

Figure 5:
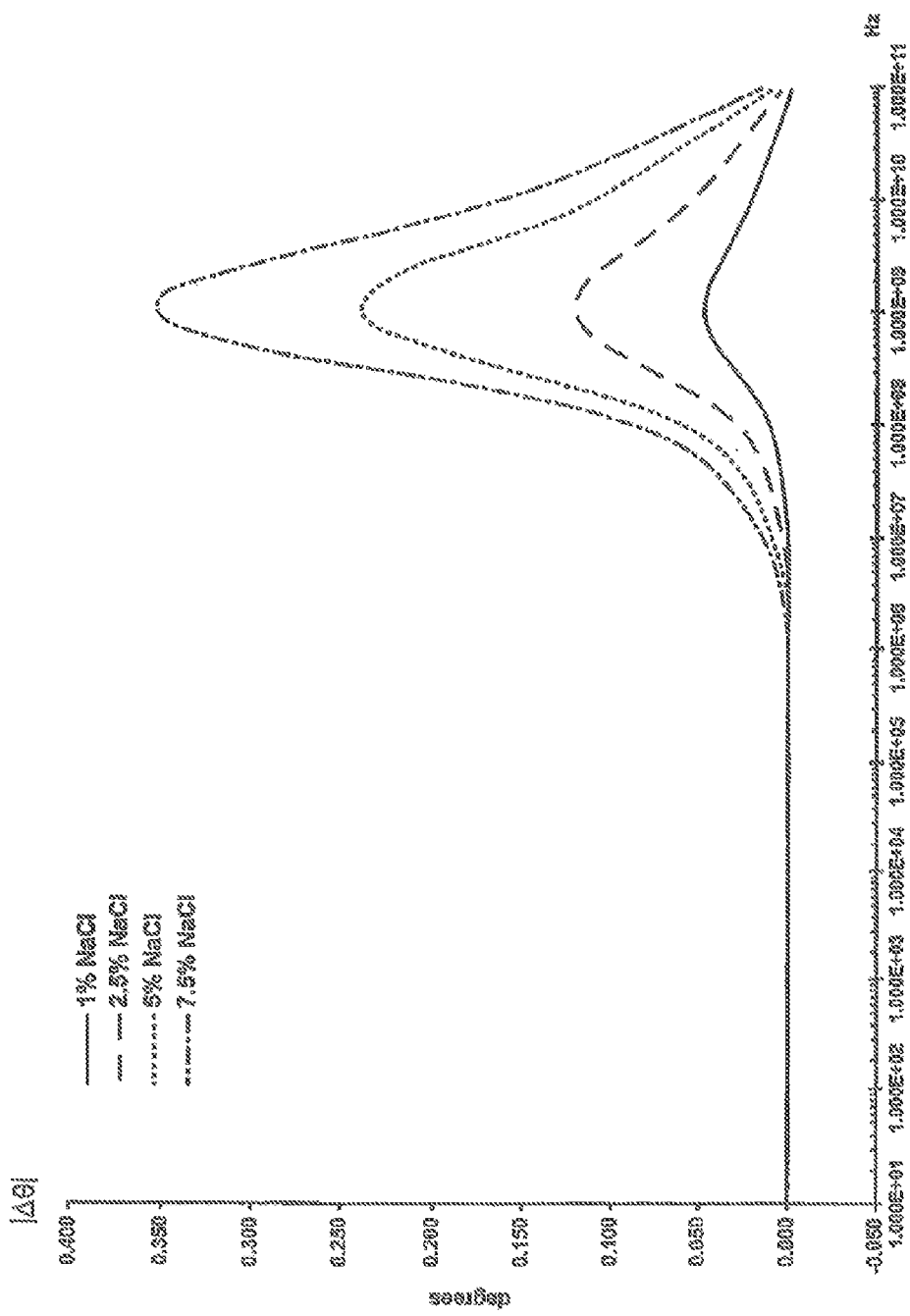
FIG. 5 is a calculated graph of phase shift vs. frequency in a simulation of intraperitoneal bleeding.

FIG. 5 is a calculated graph of phase shift vs. frequency. FIG. 5 was obtained from our theoretical calculation for gut tissue and shows the absolute homogenized values of the inductive phase shift as a function of frequency for various volumes of physiological saline into the abdominal cavity, simulating various degrees of bleeding. The results are shown in a homogenized form with respect to the values without saline. As can be seen, an increase in the volume of injected saline causes an increase in inductive phase shift. Specifically, the relative phase shift caused by internal bleeding begins at about 1 MHz. The phase shift difference due to internal bleeding has a characteristic inverse U type shape with a maximal at about 1000 MHz. The behavior shown in the figure beyond 1 GHz is highly approximate.

As can be seen, the values of the phase shift obtained from the analytical calculations provide an excellent qualitative indication of the effect of internal bleeding. Thus, the present system operates even if the bulk properties of the tissue in the abdomen are substantially different from the values that we used, since we did not consider fat, muscle, food and many other components in the abdomen. Nevertheless, the results suggest that the resolution of the measurement is greater for certain optimal values. In optional clinical applications, the phase shift can be scanned over a wide range of values to determine the best frequency for the highest signal to noise measurement.

Figure 6:
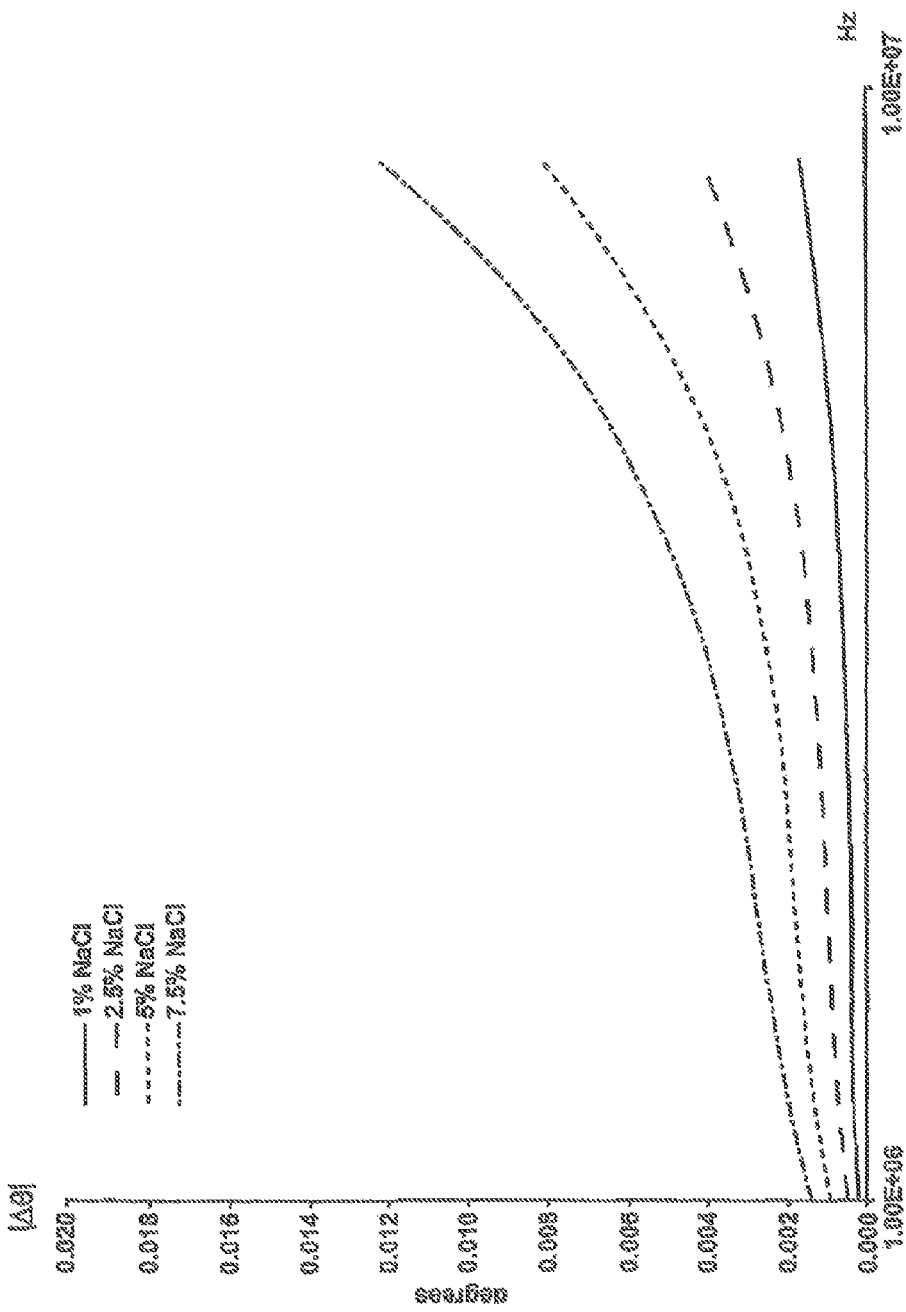
FIG. 6 is a magnified view of FIG. 5 in the frequency region from 1 to 9 MHz.

The results in FIG. 5 indicate that the phase shift due to internal bleeding should be detectable from about 1 MHz. FIG. 6 is a magnified view of the phase shift in FIG. 5 in the frequency region from 1 to 9 MHz, which confirms this. Here it is important to notice that in this range the phase shift relative to baseline increases with an increase in measurement frequency and amount of simulated internal bleeding. We have chosen this range of frequencies for our experimental studies because it is the onset of the phenomenon of phase shift due to internal edema.

Figure 7:
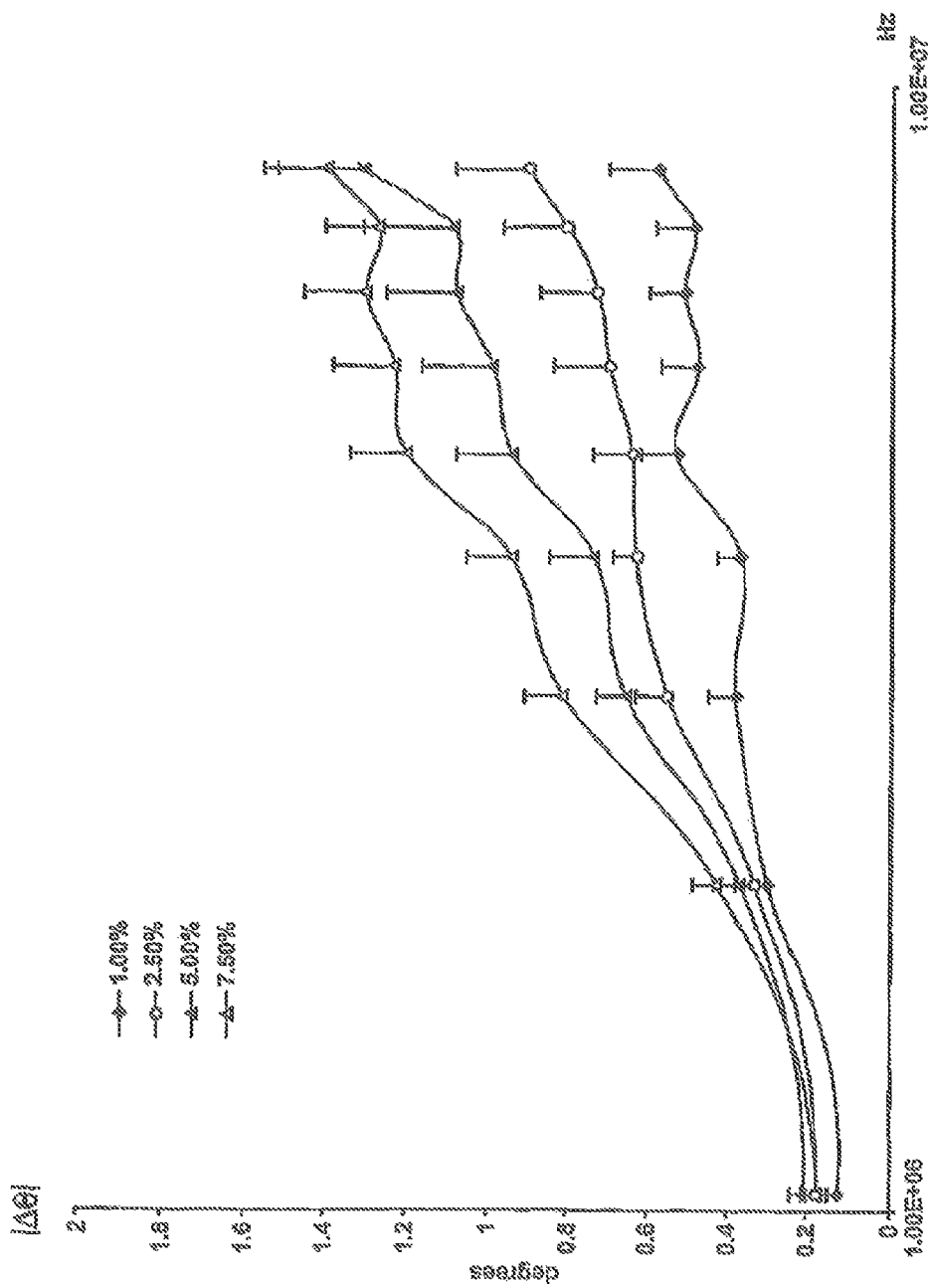
FIG. 7 is experimentally measured homogenized absolute values of the inductive phase shift as a function of frequency for various tissue volumes of saline injected into a rat abdomen. The percentage indicates the amount of saline injected relative to the total body weight of the rat. The rats used in this experiment were about 250 to 300 grin weight.

FIG. 7 shows the experimentally measured homogenized absolute values of the inductive phase shift as a function of frequency for various volumes of physiological saline into the abdominal cavity, simulating various degrees of bleeding. The results are shown in a homogenized form with respect to the control values, the baseline measurements. In this mode of presentation, the experimental subject without water produces zero phase shift at all frequencies and the injection of the physiological saline solution produces the departure from zero. Another advantage of presenting the results homogenized with respect to the control values is to overcome possible bias in the electronic circuitry. The frequency is given in a logarithmic scale from 1 to 8.5 MHz. The value of one standard error is also shown in the figure. The beating of the heart, breathing as well as abdominal motion might change the bulk electrical properties of the composite body under measurement. These factors may affect the magnitude and phase of the induced voltage at the sensing coil in the whole bandwidth. To remove natural artifacts due to physiological activity, 20 measurements were taken at each frequency. Averaging over these measurements has the effect of a robust filter to physiological activity artifacts. The figure shows that the change in phase shift due to simulated internal bleeding begins at about 1 MHz and increases with frequency and amount of internal bleeding. Qualitatively, the experimental results are very similar to the theoretical calculations.

In summary: these experimental results confirm that measuring the relative spectroscopic distribution of induction phase shift in the bulk of the abdominal cavity can be used for non-contact detection of intraperitoneal bleeding. Thus, in clinical practice, induction phase shift can be measured as a function of time and frequency in patients who are in danger of internal bleeding.

(f) Experimental Results—Detection of Brain Edema:

As will be shown herein, our results verified that bulk measurement of inductive phase shift can be used for non-contact detection of the content of water in brain, lung and muscle tissue. The analytical results of FIG. 2 showed an increase of the phase shift proportional to the water content starting at frequencies as low as 10 MHz. In addition, our results show that the phase shift changes with frequency, in a rather complex manner.

The results show that the phase shift is sensitive to the relative volume of edema at frequencies higher than approximately 10 MHz. The effect of edema on brain, lung and muscle tissues is tissue type specific. Increasing the volume of tissue has the effect of lowering the frequency at which the phase shift becomes sensitive to the volume of edema. The results indicate that bulk induction measurement of the phase shift has the potential for becoming a simple means for non-contact detection of formation of edema in brain, lung and muscle tissues.

As a first order model of edema in the brain, ex-vivo brain tissue of pig (used approximately 8 hours after the animal sacrifice) was processed through a mixer and combined with various volumes of a physiological saline solution (0.9% w/w NaCl) to form a homogeneous paste. In accordance with experiments performed by the Applicants in testing present invention, the brain conductivity data used in the relevant calculations were taken from Gabriel's experimental report for excised bovine brain tissue supra. The data for excised bovine brain tissue was obtained two hours postmortem and at body temperature. The fluid was taken as a solution of 0.9% w/w of NaCl, with a constant electrical conductivity $\sigma=1.3$ S/m and a relative permittivity $\in_r=80$.

In our preparation, the changes in the electrical properties of brain tissue with the increase in water content may be explained as the dilution of a mixture of water and the proteins present in dried tissue. In the analyzed frequency range the cellular membranes have low impedance, and the tissue may be treated as a suspension of proteins in water. The significance of this is that, in the brain, at frequencies at the high end of the beta dispersion and above our experimental model will be comparable to that in viable tissue. At frequencies at the low end of the beta dispersion a greater difference between live tissue and edematous fluid is seen, and therefore, in that range, the effect of edema is more pronounced than determined in our experiment. Therefore, the present experimental model could be considered to provide a lower limit in the sensitivity of edema detection with our techniques and we can anticipate that the detection will be even better in a living organism.

Three different volume ratios between the volume of brain tissue and of saline were evaluated: 10, 20 and 30%. The paste was placed in a cylindrical and nonmagnetic recipient made of Teflon with a radius R=7.5 cm and height t=8 cm. This volume was chosen because it is on the order of a typical adult brain volume. In addition we studied samples of pure brain tissue that was also homogenized and pure physiological saline.

A calculation of the penetration depth ($\delta$) as a function of frequency for saline and brain tissue was done according to the expression:

$$\delta = (2/\omega\mu_0\sigma)^{1/2}$$

where $\mu_0$ is the permeability of free space. We used the electrical conductivity data reported in Gabriel, supra for excised bovine brain tissue. The data for excised bovine brain tissue was obtained two hours post-mortem and at body temperature. The fluid was taken as a solution of 0.9% w/w of NaCl, with a constant electrical conductivity $\sigma=1.3$ S/m and a relative permittivity $\in_r=80$. The result shows that at 10 MHz; the skin depth is around 14 and 30 cm for pure saline and brain respectively. These values are larger than the thickness of the sample (8 cm).

All the samples were geometrical and vertically centered between excitation coil 12 and sensing coil 14. The geometrical position was carefully maintained as similar as possible for all the samples.

For every sample, twenty spectra of phase shift were obtained in the range of from 1 to 8 MHz. The data were averaged over twenty separate measurements, for each frequency. To overcome the bias in the phase shift due to the system electronics, the data were homogenized with respect to the values for brain 100%. In this way the changes observed in phase will depend essentially only on the electrical properties of the sample. The measurements were made at the room temperature (approximately 24° C.).

Figure 8:
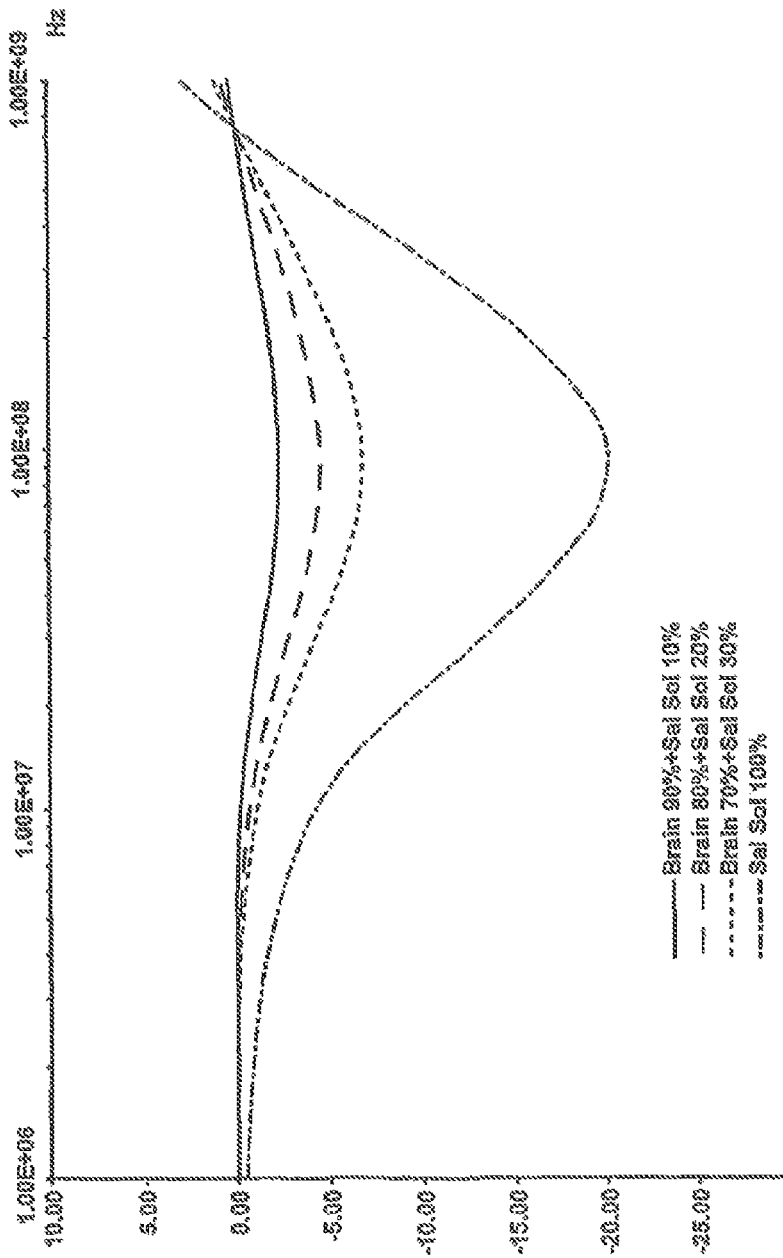
FIG. 8 is a calculated phase shift in brain tissue with various degrees of edema.

FIGS. 8 and 9 show the difference between the calculated (FIG. 8) or measured (FIG. 9) phase shift in brain tissue with various degrees of edema and the calculated or measured phase shift in the case with 100% brain tissue, as a function of frequency. In this mode of presentation brain tissue without edema produces zero phase shift at all frequencies and the addition of saline produces the departure from zero. FIG. 8 shows the calculated inductive phase shift as a function of frequency for various ratios of normal brain tissue to physiological saline, simulating various degrees of edema. The calculations were made by solving Eq. (10) and inserting in Eq. (1) brain tissue properties taken from Gabriel, supra. The edematous fluid was taken as saline (NaCl, 0.9% w/w) with a constant electrical conductivity $\sigma=1.3$ S/m and a relative permittivity $\in_r=80$. FIG. 8 shows the calculated phase shift as a function of frequency in the range of from 1 MHz to 1000 MHz. The analytical study shows that the phase shift is changing with frequency in a U shaped form and appears to have a maximum at about 100 MHz. Evidently, the phase shift increases with saline content, at any frequency. FIG. 8 shows that the phase shift can be used to measure edema in a wide range of frequencies and that there may be some optimal values of frequency that produce the highest signal.

Figure 9A:
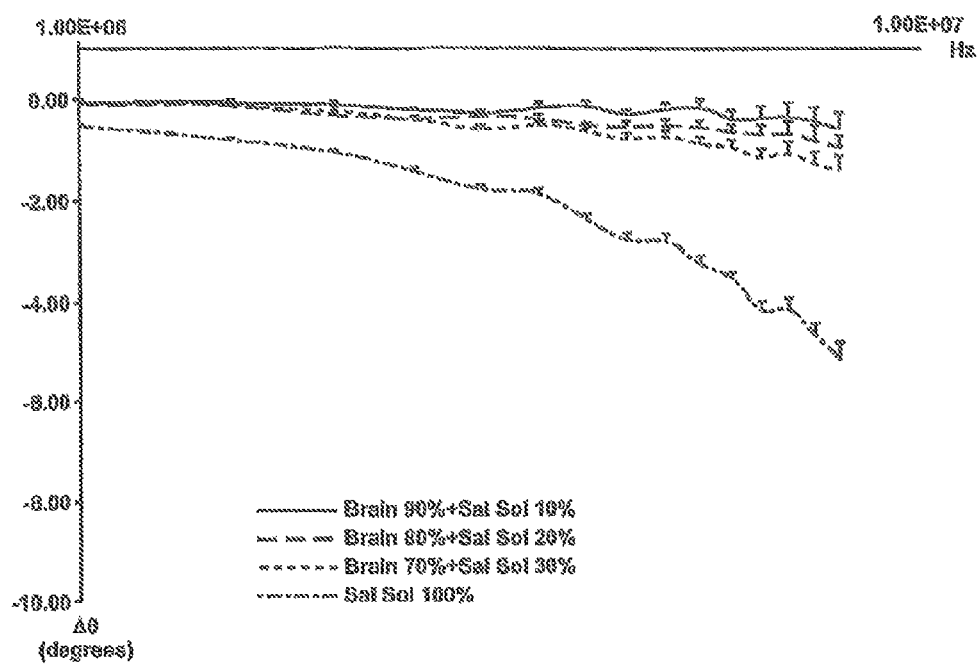
FIGS. 9a and 9b are an experimentally measured phase shift in brain tissue in vitro with various degrees of edema.
Figure 9B:
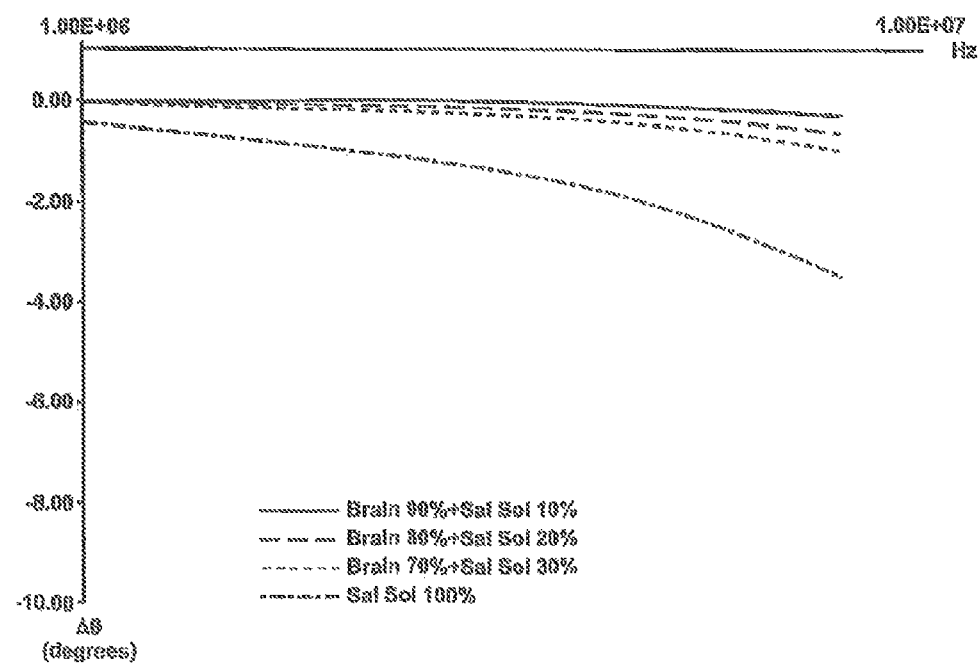

The outcome of our experiments is shown in FIG. 9A, which shows the phase shift of various compositions of brain tissue and saline as a function of frequency. Specifically, FIG. 9A shows the phase shift from three different volume ratios between the volumes of saline to brain tissue: 10, 20 and 30%. Data for 100% saline is also shown. FIG. 9B shows the part of the curve developed in FIG. 8 in the range of the experimental measurements, to 8 MHz. A comparison of FIGS. 9A and 9B shows that the experimental results are quantitatively and qualitatively similar to the theoretical predictions. The phase shift increases with frequency and with water content. The frequency is given in a logarithmic scale from 1 to 8 MHz. The value of one standard error is also shown in the figure. The error in our experimental apparatus increases with an increase in frequency for all the volume ratios of saline to brain tissue.

The data in FIGS. 8 and 9 are presented by homogenizing the measured phase shift with respect to the phase shift in the case with 100% brain tissue. Therefore, the difference between the calculated or measured phase shift in brain tissue with various degrees of edema and the calculated or measured phase shift in the case with 100% brain tissue is shown as a function of frequency.

In this mode of presentation, brain tissue without edema produces zero phase shift at all frequencies and the addition of saline produces the departure from zero. With this mode of presentation, the sensitivity of our method for detecting edema by measuring bulk phase shift becomes clear, as does the effect of measurement frequency. Another advantage of presenting the results homogenized with respect to 100% brain tissue phase shift is to overcome possible bias in the electronic circuitry. Furthermore, this homogenized mode of presentation removes any systemic errors that could be caused by the electronics circuitry producing a bias in the experimentally measured phase shift.

A further advantage of the present system is that in the analyzed frequency domain phase shift is a measure that is strongly dependent on water content in relation to organic molecular cellular contents and not on cell structure.

It is clear from FIGS. 8 and 9 that phase shift due to changes in water content is substantial and detectable. In FIGS. 8 and 9, the departure from zero is the indication for change in water content. The change in phase shift increases with frequency and with water content. The experimental results suggest that the capability of the measurement system to detect water content improves at high frequencies. For example, the phase shift value detected at 8 MHz is clearly larger for all the tested samples.

Our results also show that measurable differences in phase shift are noted between 3 MHz to 4 MHz with higher volumes of saline producing measurable phase differences at lower frequencies. Our results demonstrate that valuable information for detection of phase shift with edema can be obtained at frequencies that are three orders of magnitude lower than the microwave frequencies and in a broad range of frequencies. The curve of saline alone provides the upper limit of the expected phase shift measurement relative to pure brain tissue.

The present invention can thus be used to continuously monitor phase shift to detect worsening conditions of increase in edematous fluid in the brain. Specifically, continuously measuring the relative changes in phase shift with time would produce curves as shown in FIG. 9 in the case of formation of edema. Thus, detecting changes in phase shift could point to worsening conditions of the patient.

Extending the present study over a wider range of frequencies may also hold much information since our analytical studies predicts a non-linear behavior throughout the range from MHz to GHz.

In summary, the results of this theoretical and in vitro study provide substantive preliminary information, which suggests that measuring the relative spectroscopic distribution of induction phase shift can produce a robust means for noncontact detection of occurrence of edema in the brain.

What is claimed is:

1. A system for analyzing a tissue sample, comprising:
   a first antenna and a second antenna positioned opposite one another;
   a measurement system connected to the second antenna, wherein the measurement system is configured to measure a phase shift of a plurality of voltages between the first and second antennae at a plurality of frequencies in a frequency range.

2. The system of claim 1, wherein the first and second antennae do not contact the tissue sample.

3. The system of claim 1, wherein the measurement system is configured to determine a condition of the tissue sample by comparing the phase shift with a known normal phase shift to thereby detect at least one condition, wherein the condition is selected from the group consisting of: edema, ischemia, bleeding, dehydration, water accumulation in the tissue sample, extravasation, and disease.

4. The system of claim 1, wherein the tissue sample is selected from the group consisting of: brain tissue, lung tissue, heart tissue, muscle tissue, skin tissue, kidney tissue, cornea tissue, liver tissue, abdomen tissue, head tissue, leg tissue, arm tissue, pelvis tissue, chest tissue, and trunk tissue.

5. The system of claim 1, wherein the measurement system is further configured to determine a change in the phase shift over time.

6. The system of claim 5, wherein the measurement system is further configured to determine, based on the change in the phase shift over time, a condition of the tissue, wherein the condition is selected from the group consisting of: edema, ischemia, bleeding, dehydration, water accumulation in the tissue sample, extravasation, and disease.

7. The method of claim 6, wherein the tissue sample is selected from the group consisting of: brain tissue, lung tissue, heart tissue, muscle tissue, skin tissue, kidney tissue, cornea tissue, liver tissue, abdomen tissue, head tissue, leg tissue, arm tissue, pelvis tissue, chest tissue, and trunk tissue.

8. A system of analyzing a tissue sample, comprising:
   a first induction coil and a second induction coil positioned opposite one another;
   a measurement system connected to the second induction coil, wherein the measurement system is configured to measure an alternating current produced in the second induction coil at a plurality of frequencies in a frequency range, and determine a phase shift of a plurality of alternating currents between the first induction coil and the second induction coil at the plurality of frequencies in the frequency range.

9. The system of claim 8, wherein the first and second induction coils do not contact the tissue sample.

10. The system of claim 8, wherein the measurement system is further configured to determine a condition of the tissue sample by comparing the phase shift with a known normal phase shift to thereby detect at least one condition, wherein the condition is selected from the group consisting of edema, ischemia, bleeding, dehydration, water accumulation in the tissue sample, extravasation, and disease.

11. The system of claim 8, wherein the frequency range is between 100 kHz to 10 GHz.

12. The system of claim 8, wherein the tissue sample is selected from the group consisting of brain tissue, lung tissue, heart tissue, muscle tissue, skin tissue, kidney tissue, cornea tissue, liver tissue, abdomen tissue, head tissue, leg tissue, arm tissue, pelvis tissue, chest tissue, and trunk tissue.

13. The system of claim 8, wherein the frequency range is between 10 kHz and 10 GHz.

14. The system of claim 8, wherein the frequency range is between 1 MHz and 10 GHz.

15. The system of claim 8, wherein the measurement system is further configured to determine a condition of the tissue sample by comparing the phase shift with a known normal phase shift to thereby detect interperitoneal bleeding in the tissue sample, and wherein the frequency range is between 100 kHz to 10 GHz.

16. The system of claim 8, wherein the measurement system is further configured to determine a change in the phase shift over time.

17. The system of claim 16, wherein the first and second induction coils do not contact the tissue sample.

18. The system of claim 16, wherein the measurement system is further configured to determine, based on the change in the phase shift over time, a condition of the tissue, wherein the condition is selected from the group consisting of edema, ischemia, bleeding, dehydration, water accumulation in the tissue sample, extravasation, and disease.

19. The system of claim 16, wherein the tissue sample is selected from the group consisting of brain tissue, lung tissue, heart tissue, muscle tissue, skin tissue, kidney tissue, cornea tissue, liver tissue, abdomen tissue, head tissue, leg tissue, arm tissue, pelvis tissue, chest tissue, and trunk tissue.

* * * * *